United States Patent [19]
Barbour

[11] Patent Number: 6,081,322
[45] Date of Patent: Jun. 27, 2000

[54] NIR CLINICAL OPTI-SCAN SYSTEM

[75] Inventor: Randall L. Barbour, Westbury, N.Y.

[73] Assignee: Research Foundation of State of New York, Albany, N.Y.

[21] Appl. No.: 08/951,892

[22] Filed: Oct. 16, 1997

[51] Int. Cl.$^7$ ................................. G01N 21/00
[52] U.S. Cl. ................. 356/73.1; 356/376; 356/337
[58] Field of Search .................. 356/376, 337, 356/73.1

[56] References Cited

U.S. PATENT DOCUMENTS

| | | | |
|---|---|---|---|
| 5,137,355 | 8/1992 | Barbour et al. | 356/342 |
| 5,213,105 | 5/1993 | Gratton et al. | 128/664 |
| 5,625,458 | 4/1997 | Alfano et al. | 356/446 |
| 5,664,574 | 9/1997 | Chance | 128/664 |

FOREIGN PATENT DOCUMENTS 0 614 645 A1  3/1994  European Pat. Off. ........ A61B 10/00

OTHER PUBLICATIONS

Application of the zooming method in near–infrared imaging; M.R. Jones et al; Physics in Medicine and Biology, vol. 42, No. 10, Oct. 1997, pp. 1993–2009.

PCT Search Report, Jan. 21, 1999 (PCT/US98/20810).

*Primary Examiner*—Frank G. Font
*Assistant Examiner*—Reginald A. Ratiff
*Attorney, Agent, or Firm*—Morgan & Finnegan LLP

[57] ABSTRACT

The present invention relates to three-dimensional optical imaging techniques and, more particularly, to the detection and three-dimensional imaging of absorbing and/or scattering structures in complex random media, such as human body tissue, by detecting scattered light emerging from the medium. An apparatus for optical tomographic imaging of tissue structures with non-uniform surface geometries in accordance with the invention comprises: an optical source capable of providing light having a wavelength capable of at least attenuated transmission through the tissue; a fiber array consisting of fiber bundles for transmitting light from the optical source to the tissue to be imaged, and a second fiber array consisting of fiber bundles for receiving light scattered by the tissue; an adjustable assembly comprising an adjustable support member supporting one end of each fiber bundle, the fiber bundles being distributed along the portion of each support member which conforms to a surface of a specimen being imaged so as to transmit light into, and collect light emanating from, the surface of the imaged tissue at a multitude of spaced-apart points; and a detector array receiving light collected by the fibers in the second fiber bundle.

32 Claims, 6 Drawing Sheets

NIR CLINICAL OPTI-SCAN SYSTEM

The U.S. Government has a paid-up license in this invention and the right in limited circumstances to require the patent owner to license others on reasonable terms as provided for by the terms of Contract CA59955-01 awarded by National Institutes of Health and Contract N000149510063 awarded by Office of Naval Research.

FIELD OF THE INVENTION

The present invention relates to three-dimensional optical imaging techniques and, more particularly, to the detection and three-dimensional imaging of absorbing and/or scattering structures in complex random media, such as human body tissue, by detecting scattered light emerging from the medium.

BACKGROUND OF THE INVENTION

Most medical diagnostic equipment capable of providing a three-dimensional image of an interior region of the human body is extremely bulky and costly. The space requirements and costs associated with Magnetic Resonance Imaging (MRI) equipment sometimes render it an impracticable diagnostic option, even when a three-dimensional image is required for proper diagnosis. Conventional computer-aided tomography (CAT) scanning systems, aside from being bulky and expensive, additionally require the exposure of the patient to potentially harmful radiation.

Optical methods for the detection and identification of objects embedded in scattering media, such as human tissue, are desirable because optical systems can be compact, light-weight, and relatively inexpensive while also eliminating the need for radiation from harmful portions of the electromagnetic spectrum. Optical systems are also capable of determining the chemical makeup of a structure by performing a spectral analysis, a capability which is not available from MRI or CAT imaging systems.

One problem with optical systems for medical applications is that the human body is a turbid, or scattering, medium which causes incident light to be diffusely directed away from a target object, thus obscuring the location and surface topology data from the object. A successful optical diagnostic tool for imaging objects embedded in turbid media must be able to extract useful information from the multiply-scattered light signals reflected from the embedded target.

Barbour, et al., U.S. Pat. No. 5,137,355 entitled "Method of Imaging a Random Medium," (hereinafter the "Barbour '355 patent") is incorporated by reference herein. This patent discloses a non-invasive medical imaging technique based on the measurement of scattered light in the near-infrared (NIR) region of the electromagnetic spectrum, where significant penetration into body tissues occurs. Prior to the foregoing technique, much work had been done on the optical detection of targets in turbid media, but the problem of imaging the depth or structure of an embedded object remained. The technique of the Barbour '355 patent allowed an observer to accurately detect, three-dimensionally image, and spectroscopically characterize target objects located within a turbid medium.

The technique disclosed in the Barbour '355 patent employs a multi-wavelength collimated source and a collimated receiver and performs a positional and angular scan of the scattered light from the specimen for each position of the incident beam. The technique allows the determination of an object's depth, structure, and absorptive and scattering properties within the turbid medium.

The methodology set forth in the Barbour '355 patent represents a basic description concerning how to recover images of the interior structure of highly scattering media. The only requirement is that it expects the detected signal to have undergone sufficient scattering such that every propagation is accurately described according to a particle picture (i.e. the radiation transport equation). Thus, this methodology holds for any type of energy source (e.g. electromagnetic, acoustic, particle beam) and for any source condition (i.e. DC, time resolved, or AC) in terms of assessment of the temporal characteristics of the propagating signal. While this methodology is correct in general terms, it does not speak to specific details regarding how best to perform a measurement, in particular, under non-ideal conditions.

For example, a preferred requirement for the construction of a high-quality image is the elimination of such non-ideal factors as motion artifacts, arising from unavoidable motion caused by respiration and heartbeat from the patient.

SUMMARY OF THE INVENTION

The present invention is directed to an improved optical imaging apparatus and technique for imaging non-uniform specimen geometries and which minimizes motion artifacts.

An apparatus for optical tomographic imaging of tissue structures with non-uniform surface geometries in accordance with the invention comprises: an optical source capable of providing light having a wavelength capable of at least attenuated transmission through the tissue; a fiber array consisting of fiber bundles for transmitting light from the optical source to the tissue to be imaged, and a second fiber array consisting of fiber bundles for receiving light scattered by the tissue; an adjustable assembly comprising an adjustable support member supporting one end of each fiber bundle, the fiber bundles being distributed along the portion of each support member which conforms to a surface of a specimen being imaged so as to transmit light into, and collect light emanating from, the surface of the imaged tissue at a multitude of spaced-apart points; and a detector array receiving light collected by the fibers in the second fiber bundle.

Several optical sources are suitable for use in the apparatus, including diode lasers, Ti:Sapphire lasers, dye lasers, multi-wavelength lasers, continuous-wave (CW) lasers, and pulsed-power lasers. In the preferred embodiment of the invention, the optical source emits light in the near infrared portion of the electromagnetic spectrum. The fiber array has translatable light-receiving ends adjacent to the light source.

In a preferred embodiment, the apparatus incorporates a focusing lens disposed between the optical source and the fiber array. In addition, the adjustable support member may be constructed of deformable material having plastic memory, or comprised of mechanical elements forming one or more concentric adjustable irises. The preferred embodiment also incorporates an attenuator disposed between the second, light receiving fiber array and the detector array to control the dynamic range of the light collected from the specimen.

The further features, aspects and advantages of the invention will be better understood from the following detailed description of the preferred embodiment and accompanying drawings.

DETAILED DESCRIPTION OF THE PREFERRED EMBODIMENTS

In accordance with one aspect of the present invention, an optical imaging apparatus is provided that allows the three-dimensional imaging of non-uniform geometries. In its present form, the apparatus can be configured to optimize the collection of scattered light from non-planar specimens and is capable of reducing motion artifacts by creating a conformal structure which surrounds and confines the non-uniform body geometry under test, thus providing stabilization as well as precise geometrical information which is needed for the image processing.

In its preferred embodiment, the present invention detects light scattered from an optical inhomogeneity, such as a tumor, located within an optically dispersive medium such as normal human tissue. The source fibers direct light towards a target medium (i.e., body tissue) via a conformal structure. Light propagating through the medium will experience multiple scattering prior to emerging. Emerging light is collected by receiving fiber bundles also contained within the conformal structure.

The present invention characterizes the relative contribution of emerging light from each portion of the target medium from which light is scattered. The characterization takes into account the depth of the target portion being evaluated as well as the distance and angle of the receiving fibers relative to the source fibers. The target data is determined based on prior calibrated measurements of position-dependent flux information from scattering media; precise knowledge of source and receiver fiber positions relative to the target is therefore crucial. The conformal structure of the present invention improves the accuracy of this position information compared to prior art designs. Once the relative contributions from each target portion are determined, this information is used to reconstruct a three-dimensional image using a computer.

Figure 1:
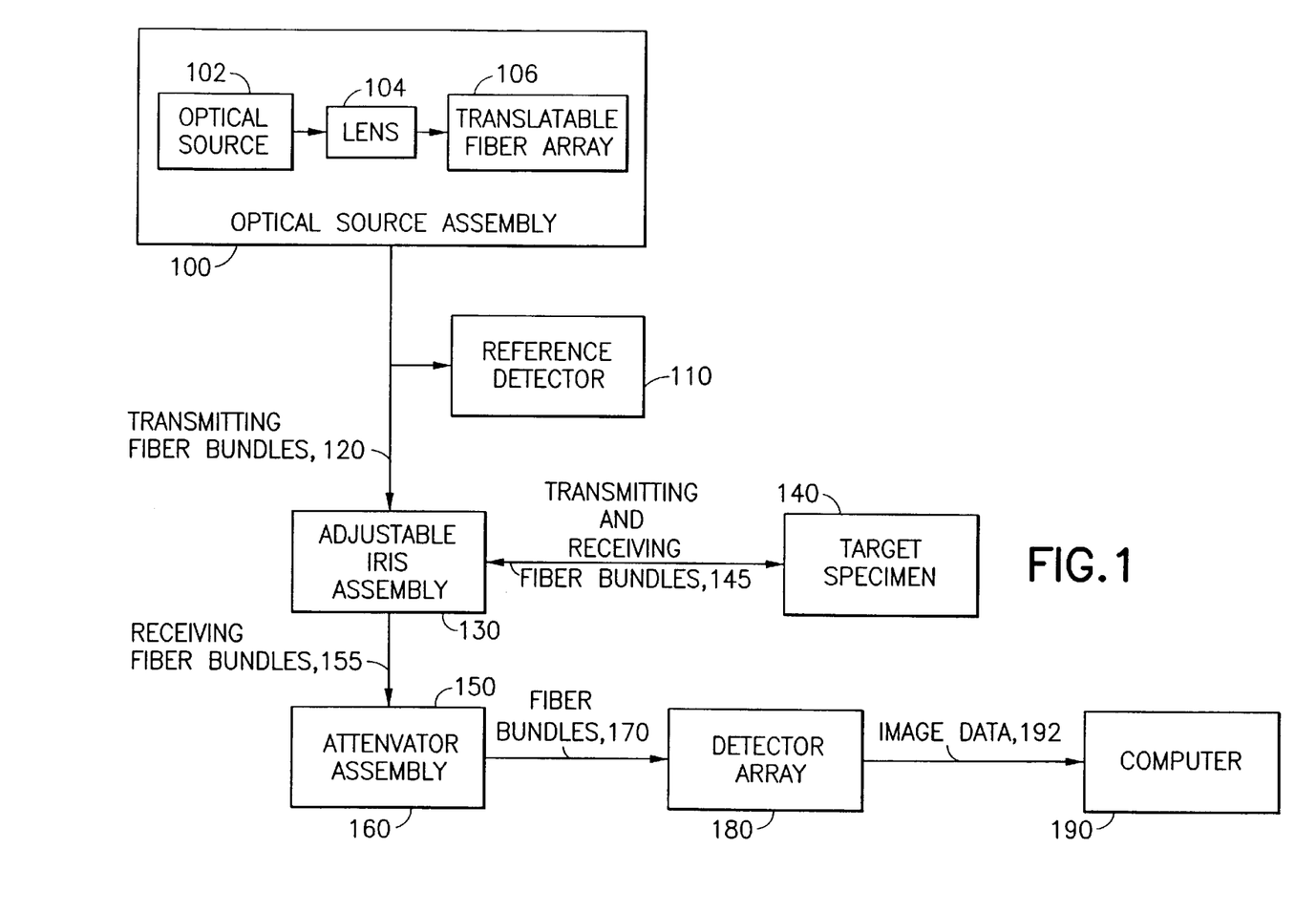
FIG. 1 is an overall system block diagram of the NIR clinical opti-scan system incorporating the invention.

FIG. 1 is an overall system block diagram of the preferred embodiment of the NIR clinical optical scanner incorporating the invention. The system comprises an optical source assembly 100, an adjustable iris assembly 130, an attenuator assembly 160, a detector array 180, and a computer 190. The optical source assembly 100 includes a near-infrared source 102, a focusing lens 104, and a translatable fiber array 106. A portion of the light emerging from the optical source assembly 100 is diverted to a reference detector 110 so that fluctuations in the source power level may be monitored and corrected. The remaining portion of the light is directed to the adjustable iris assembly 130, which houses transmitting and receiving fiber bundles 145 for directing and collecting light at the target specimen 140.

In the preferred embodiment, the adjustable iris assembly 130 comprises a plurality of conformal iris diaphragms (not shown) which adjust to fit the specific surface geometry of the target specimen 140. The conformal iris diaphragms house the distal ends of the transmitting and receiving fiber bundles 145 which send and receive light from the target specimen 140. In an alternative embodiment, the adjustable assembly is constructed of a deformable material. Light collected by the receiving fiber bundles 155 is directed to the attenuator assembly 160 so that the wide dynamic range of scattered light intensities emerging from the target specimen 140 may be adjusted. The attenuator assembly 160 comprises a plurality of attenuators of varying optical strength. In one embodiment of the invention, the attenuators are neutral density filters. In another embodiment, the attenuators are polarizers.

After passing through the attenuator assembly 160, the light is directed to the detector array 180, which is preferably a standard CCD array. The electrical signals representing the three-dimensional image information from the detector array 180 are sent to the computer 190 for image reconstruction. The system is distinguished in part from the one shown in the '355 patent discussed above in the manner in which imaging light is directed to and collected from the medium being analyzed.

Figure 2A:
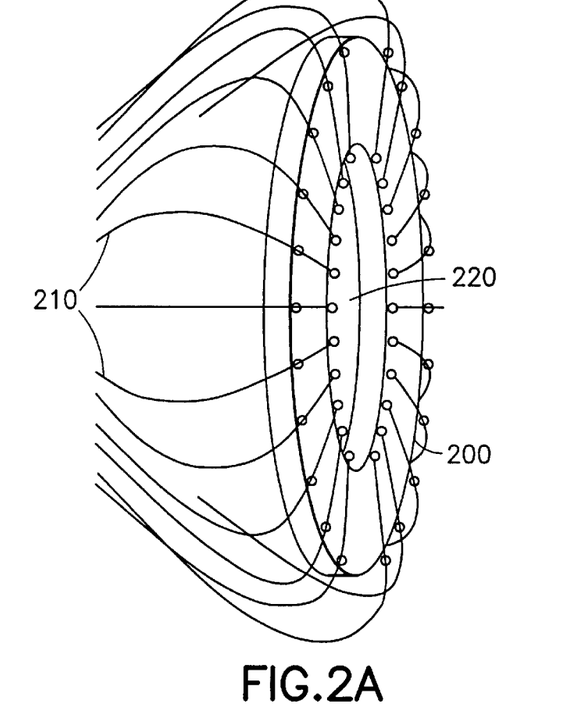
FIG. 2A is an expanded perspective view of an adjustable iris diaphragm according to the invention.
Figure 2B:
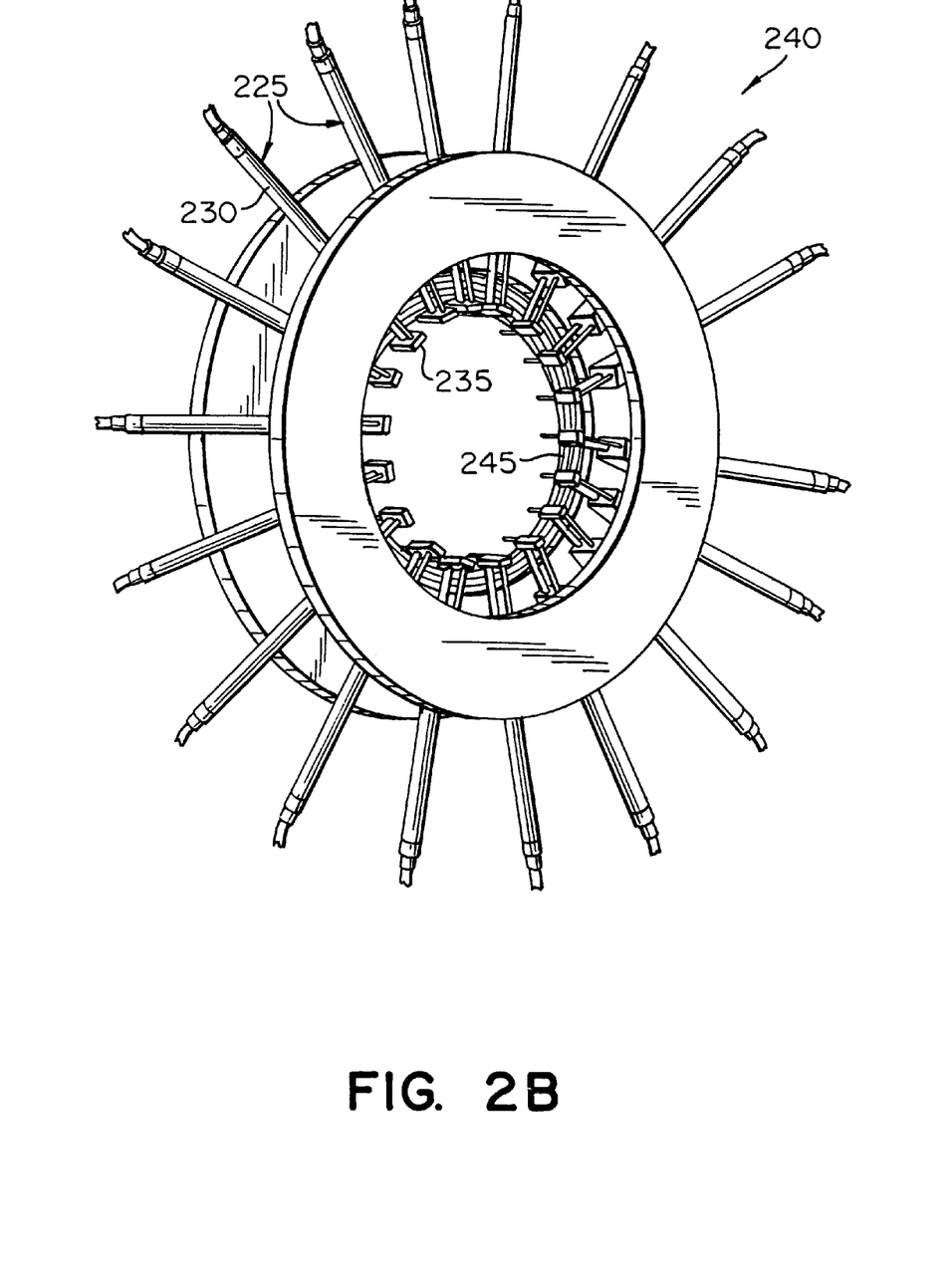
FIG. 2B is a perspective view of an adjustable iris assembly according to the present invention.

FIG. 2A shows an expanded perspective view of an adjustable iris diaphragm 200, including transmitting/receiving bundles 210, and iris opening 220. FIG. 2B is a perspective view of an adjustable iris assembly 240. Transmitting receiving bundles 210 are shown in more detail as indicated by exemplary bundle 225. There are eighteen transmitting/receiving bundles 225 shown in FIG. 2B. Transmitting/receiving bundles 225 are rigidly supported by support structures 230 and 235; support structure 230 connects transmitting/receiving bundles 225 to diaphragm 245 and support structure 235 brings transmitting/receiving bundles 225 into contact with the specimen under test (not shown). Diaphragm 245 adjusts to snuggly conform to the specimen under test.

Figure 2C:
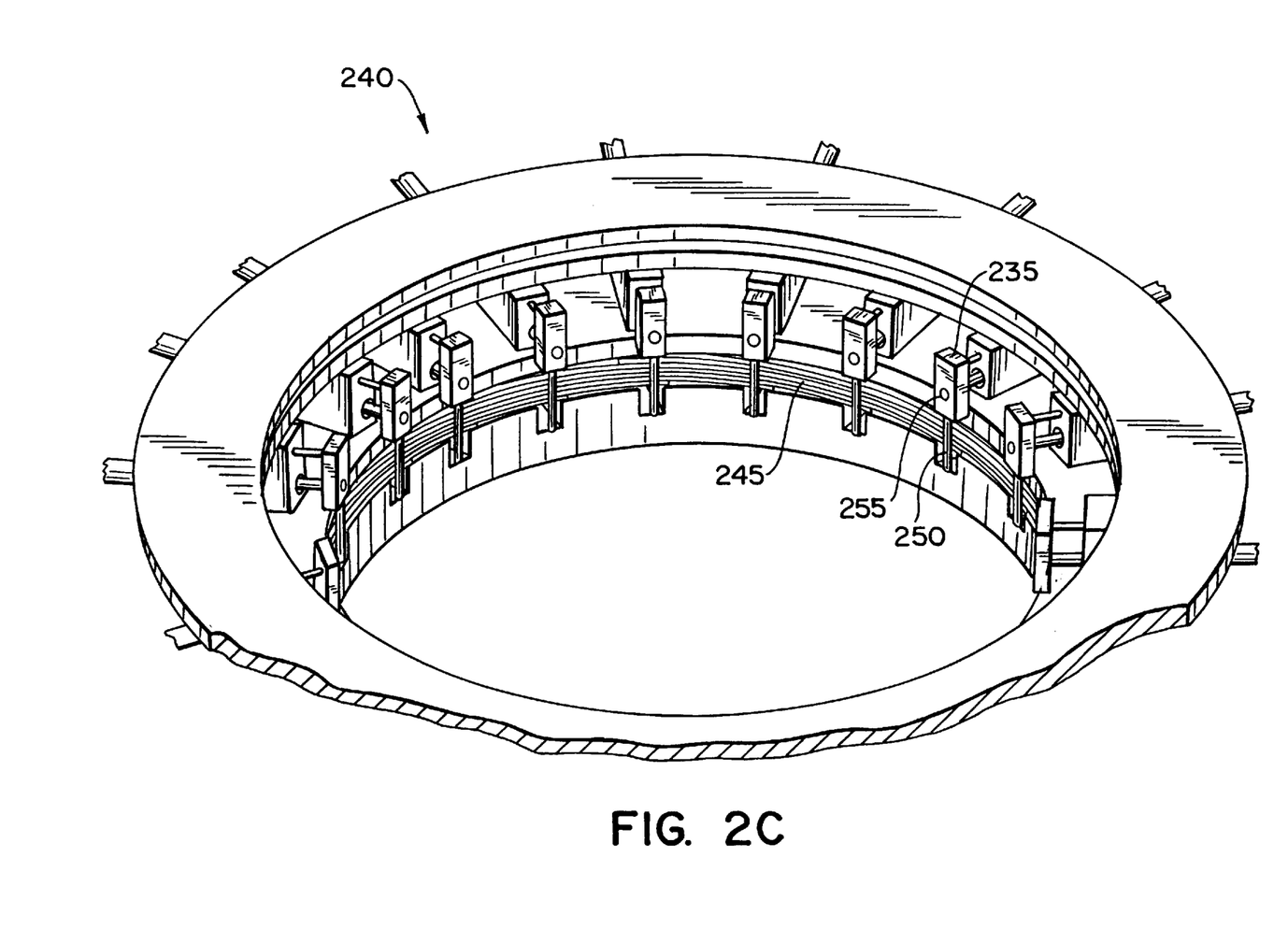
FIG. 2C is a close-up perspective view of an adjustable iris assembly according to the present invention.

FIG. 2C is a close-up perspective view of an adjustable iris assembly 240. Support structures 235 are shown in detail with metal rods 250 extending below fiber ports 255 to ensure that all supports 235 move together when diaphragm 245 is opened or closed. Diaphragm 245 can be constructed, for example, from a series of partially overlapping flexible steel plates, to which rods 250 are attached such that the degree of overlap of the flexible steel plates controls the diameter of the iris opening. Numerous other structural alternatives are available for achieving this adjustability.

In an alternative embodiment, the iris consists of a fixed supporting frame where supports 235 are axially and individually movable towards or away from the opening. Peripheral conformity of bundle terminations is achieved by individually moving the supports 235 into contact or close proximity with the tissue to be imaged.

Figure 3:
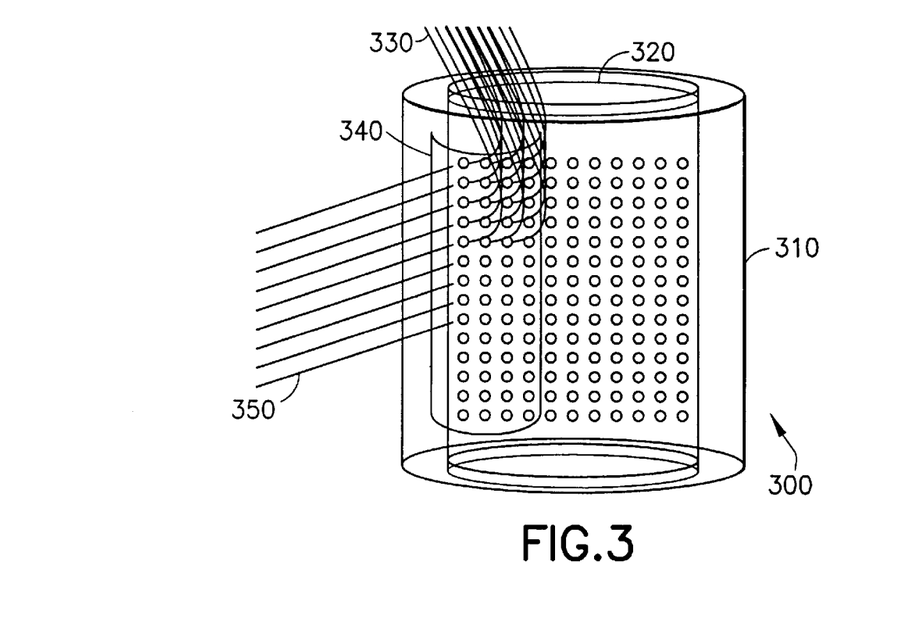
FIG. 3 is a perspective view of an attenuator assembly.

FIG. 3 shows attenuator assembly 300, including outer cylinder 310, inner cylinder 320, receiving bundles 330, attenuators 340, and transmitting bundles 350.

Figure 4A:
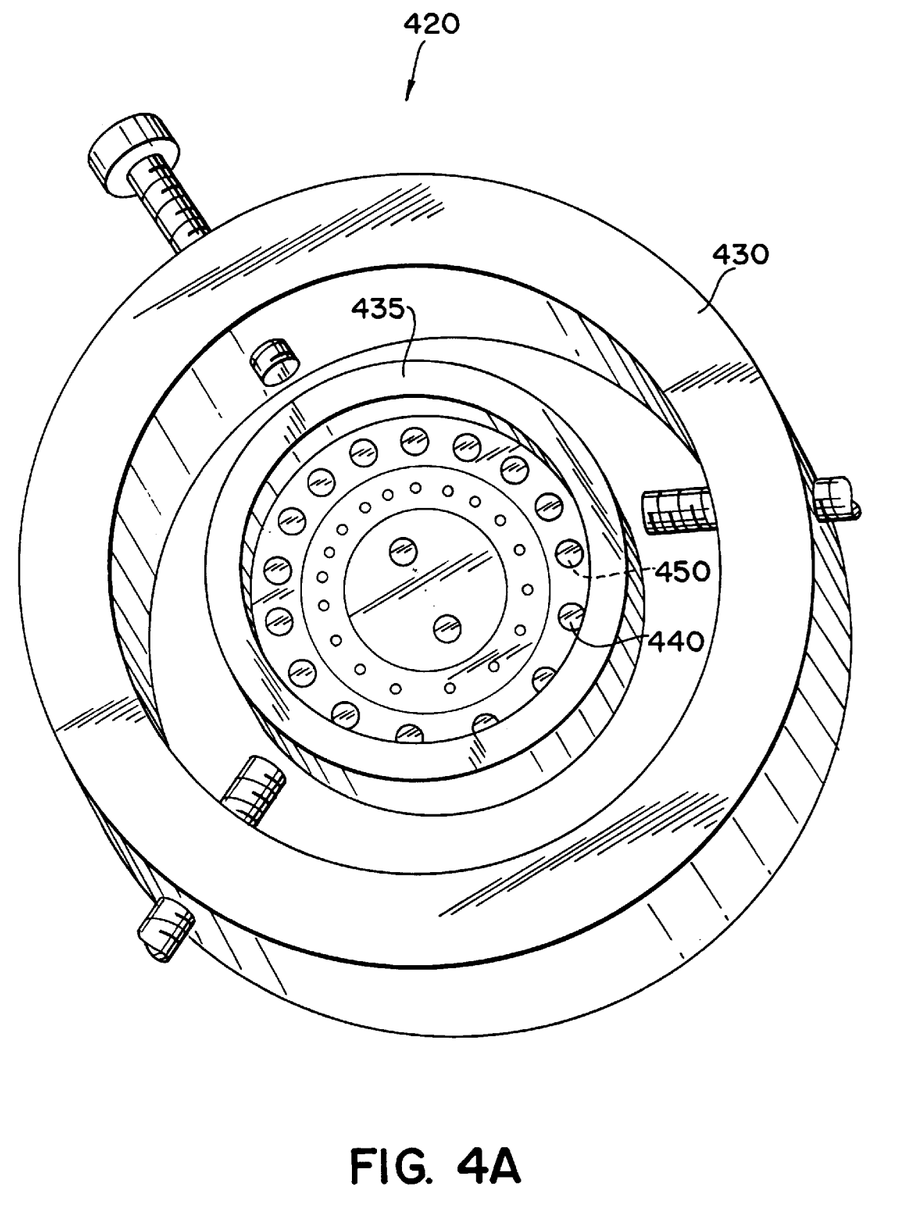
FIG. 4A is a top view of an output coupler according to the present invention.
Figure 4B:
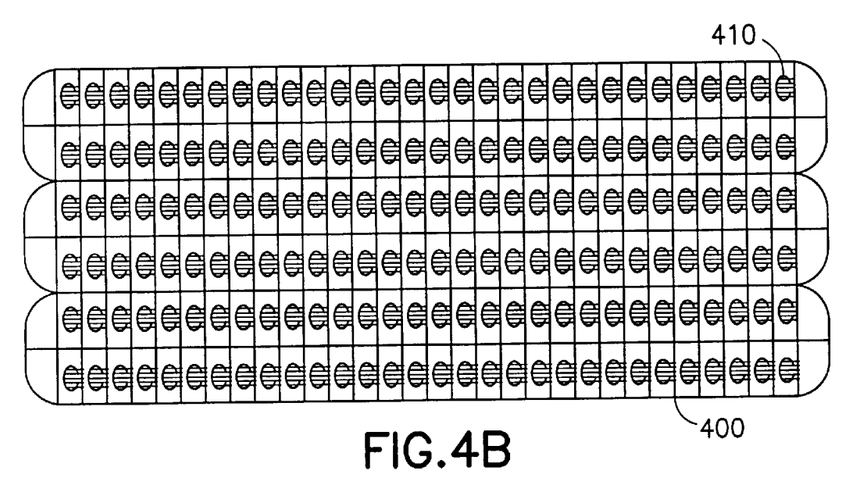
FIG. 4B is a diagrammatic representation of a detector array.

FIG. 4B shows detector array 400 with mounted transmitting bundles 410.

Figure 5A:
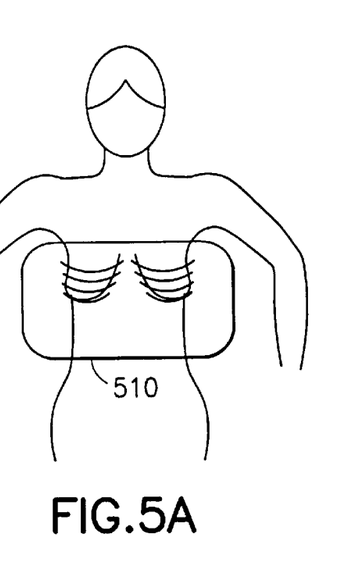
FIG. 5A is a front view of the embodiment of the invention as a dual breast scanner.
Figure 5B:
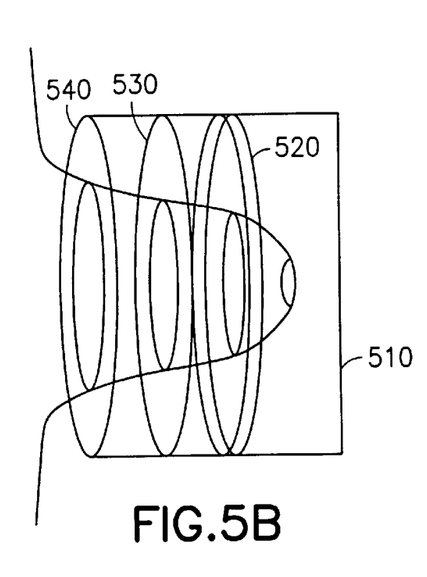
FIG. 5B is an expanded side view of one of the scanning heads of the dual breast scanner depicted in FIG. 5A.

FIG. 5A is a front view of the embodiment of the invention as a dual breast scanner, showing dual scanning heads 510. FIG. 5B is an expanded side view of one of the scanning heads 510, including adjustable irises 520, 530, and 540.

Optical source assembly 100 provides NIR light for illumination of the specimen under examination. A variety of NIR lasers 102 are available, such as diode lasers, Ti-Sapphire, and dye lasers, among others, ranging from CW operation to ultrashort temporal pulses. Coupling of the laser light into fiber array 106 is achieved by focusing the light onto the proximal ends of the fibers using focusing lens 104. The mechanically driven translatable fiber array 106 contains a minimum of 100 jacketed fiber bundles 120, each containing multiple small-diameter fibers (<200$\mu$) with a total active surface area of at least 2 mm$^2$.

Transmitting fiber bundles 120 are employed to deliver the NIR laser light to various positions within the adjustable iris assembly 130 via transmitting/receiving bundles 120.

Adjustable iris assembly 130 includes several parallel adjustable iris units, each housing a minimum of 20 transmitting/receiving bundles 120. Adjustable iris assembly 130 is rigidly fixed to an outer housing that serves to exclude ambient light. One of the individually adjustable iris diaphragms contained within assembly 130 is shown in FIGS. 2A, 2B, and 2C. These diaphragms snugly conform to the target specimen located in opening 220, where transmitting and receiving fiber bundles 210 direct and collect light.

When light is scattered from a dense object such as a tumor, embedded in a highly scattering medium such as human tissue, there is a large dynamic range of emergent signal levels. The strongest signals will be those which are directly backscattered in the vicinity of the source; signals which are scattered at oblique angles and undergo multiple reflections within the tissue will be considerably weaker than the directly backscattered signals. Attenuation of some emerging signals will therefore be required, in particular those nearby an incident source of light. For tomographic measurements, the location of these will vary with the position of the light source.

Selective attenuation of specified fiber bundles can be efficiently accomplished for any light source position using attenuator assembly 300 depicted in FIG. 3. Attenuator assembly 300 is comprised of two stationary concentric cylindrical housings, outer cylinder 310 and inner cylinder 320, between which is a rotating structure containing a plurality of attenuators 340. In one embodiment of the invention, the attenuators are graded neutral density filters. In another embodiment of the invention, the attenuators are polarizers.

Referring to FIG. 3, the inner cylinder 320 houses the distal ends of receiving bundles 330 coming from adjustable iris assembly 130; these bundles deliver the light signals collected from the target specimen 140. Light emerging from receiving bundles 330 gets selectively attenuated by attenuators 340. Outer cylinder 310 houses transmitting bundles 350 that collect the light emerging from attenuators 340 and direct the attenuated light to detector array 400 shown in FIG. 4B via the output coupler shown in FIG. 4A.

In FIG. 4A, output coupler 420 is held by outer mount 430 and inner mount 435. Inner mount 435 holds fiber bundles 450 in place via mounting screws 440. Fiber bundles 450 send light from the attenuator assembly 300 to the detector array 400.

In another embodiment, improved signal strength is achieved by positioning a lens (not shown) inside outer cylinder 310 to refocus divergent light from receiving bundles 330 onto the proximal ends of transmitting bundles 350. In yet another embodiment of the invention, for fluorescent applications, a wavelength-selective filter can also be added between receiving bundles 330 and transmitting bundles 350 to block the excitory field.

Light collected by transmitting bundles 350 from attenuators 340 is directed to detector array 400 shown in FIG. 4B.

Depending on the type of laser 102 and expected clinical application, any of a number of optical detectors or detector arrays 400 can be employed. A cooled linear CCD array is appropriate for most applications. As would be apparent to one skilled in the art, a suitable structure (not shown) attached to the front of the detector array 400 would maintain the ends of the transmitting bundles 350 in a fixed position with respect to the detector array 400 so that accurate position information is obtainable.

According to a further aspect of the invention, the outer housing consists of black plastic designed to shield the internal parts of the invention from ambient light. Another embodiment of the invention includes a rubber dam that can form a water-tight seal to a particular extremity, enabling filling of the chamber with a scattering fluid. The rubber dam and scattering fluid improve the boundary matching conditions between the fibers and the specimen required for computation of the image.

In an alternative embodiment of the invention, when appropriate, a dual-head scanner can be employed to permit differential measurements of bilateral appendages (e.g., breasts, limbs). FIG. 5A shows a front view of a dual breast scanner. In this embodiment, the invention consists of a dual-head scanner 510 containing two adjustable iris assemblies 130 and would conform to both of the patient's breasts simultaneously. FIG. 5B shows an expanded side view of one of the heads of the dual-head scanner 510 showing three adjustable irises 520, 530, and 540 for illustrative purposes.

The measured signal obtained from detector array 400 is digitized and sent to a host computer that also controls operation of the electronics, source translation, and position of attenuators 340. The host computer also is used to compute the reconstructed images and for image display.

Image reconstruction is achieved using the methods described previously in U.S. Pat. No. 5,137,355. These consider modeling of photon transport using a particle model and analyze the measured data using any one of a number of available algebraic solvers that evaluate a linear perturbation model.

In another embodiment of the invention, optical source unit 100 contains a multi-wavelength source or sources. In yet another embodiment of the invention, the scanner is operated in fluorescence-detection mode.

Among the principal attributes of the current invention is the capability of stabilizing the target structure against motion artifacts while simultaneously gently conforming it to a regular geometry. The latter is advantageous because of the expected improved efficiency gained in numerical computations when evaluating structures having regular vs. arbitrary boundaries. In addition, other design features include the ability of the measurement head to allow for gentle contact measurements (i.e., severe compression is unnecessary) and the geometrical adaptability of the unit which enables it to interface with a variety of body structures.

In the preferred embodiment the latter is accomplished using a mechanical iris to which are attached optical fibers. Adjustments of the opening of the iris can be accomplished using motion-control devices under complete control. In addition, the iris head is easily expanded to include an array of spaced apart irises, arranged in substantially parallel planes for example, allowing for facial measurement of 3-D structures.

Optical energy, for example from a laser source, is introduced into an optic fiber that terminates at the iris unit. This can be accomplished in various ways. In one embodiment the transmitting fibers are positioned in a circular arrangement housed in a cylindrical structure inside which is positioned a rotating prism under computer control which deflects the light into the fiber. The fibers could be a bundle or consist of a single fiber having a moderately large diameter (~1 mm). In either case these would be jacketed to protect from ambient light. Within the iris unit, receiving fibers are also located. The terminal ends of these fibers can be positioned adjacent to the respective light-emitting ends of the transmitting fibers, or at other locations. The precise geometry of transmitting-receiving fiber arrangement is not critical, it only needs to allow for acquiring adequate views for either source fiber.

In the preferred embodiment we have chosen to use bifurcated fibers arranged in a "bulls-eye". The central portion of the "eye" contains the transmitting fiber bundles; the "halo" contains the receiving fibers. The iris head itself could consist of a single or a multiple units. In the latter case, light entering at any location within the array would result in light exiting the target tissue at all locations. The received light is then transmitted through the receiving fibers to a filter unit that serves to attenuate expected high intensity signals present in the vicinity of any source fiber.

To accommodate repositioning of the source, the filter unit must also be repositioned. This is accomplished using a movable filter array whose position is synchronous to the location of the source fiber. In one embodiment there are two fixed nested cylinders, one that houses fibers from the iris unit and an opposing set that houses receiving fibers positioned a short distance away. In between is located a movable filter array whose positioning is synchronized with the source fiber. In another embodiment of the filter unit, fibers from the iris unit and opposing receiving fibers are housed in circular disks in between which is a rotating filter array. In either embodiment, attenuation of the received signal would usually only be required for signals near a source, although attenuation of signals from more distant fibers can be implemented if necessary or desirable. Of course, those receiving fibers opposite a source fiber will have much lower intensities and for these cases additional signal attenuation would be unnecessary and normally undesirable.

Light passing through the filter unit is then directed to an optical detector. Here again, many representations could be employed. In one case, individual detectors could be positioned so as to directly receive light passing through the rotating filter. In another case, light transmitted to opposing receiving fibers in the filter unit could be interfaced to a fiber taper whose narrow end is placed in contact with a area detector such as a 2-D CCD or CID detector.

The described system can be appropriately viewed as presenting a geometrically adaptive interface device. At one end is a light source, at the other end is a detector. In between is the iris unit and accompanying devices needed to direct light to the iris and perform any required signal conditioning (i.e. attenuation). Thus, this unit can easily accommodate any light source condition such as DC, amplitude modulated or pulsed sources. It also easily accommodates any detector appropriate for the source condition chosen.

In practice, the iris unit itself is preferably housed within a shell, shielding it from ambient light. It also could be constructed to permit the introduction of a scattering fluid into the iris head, thereby simplifying boundary conditions. In the latter case, a liquid tight seal, in the form of a rubber arm, would be required that interfaced with the target tissue.

Measured data acquired from the described device is subsequently analyzed as previously outlined in the Barbour '335 patent. Basically, nearly any type of perturbation method could be adopted. Typically, these implement some type of algebraic reconstruction method. Solutions could be limited to the First-Order Bova or Rytov approximation, or iterative Newton-type solutions could be adopted. As recognized, in the latter case, measurement data acquired from a regular geometry can be more efficiently analyzed than data from an object having arbitrary boundaries. This is one important feature accomplished with the iris unit of the invention.

Apart from analysis of the measured data to reconstruct an image, it is also understood that the data can be independently analyzed according to a feature extraction program. Basically, it is recognized that because the external geometry of a test object (i.e., a breast) is fixed and known, this tends to limit the number of possible patterns within a tomographic data set. A priori, it is reasonable to expect that different pathologies will have different influences on light propagation in the tissue. Should the external geometry of the target be highly restricted (i.e., a circle) then the range of possible patterns within the data could be similarly restricted. Thus, apart from guarding against motion artifacts, the iris unit naturally enables measurement of data that is well suited for analyzing an image recovery problem as a feature extraction problem. Feature extraction is easily evaluated using standard neural network schemes, such as back propagation. The training vectors (i.e., normalcy data) in this case would be derived from measurements performed on patients having known, well defined pathologies.

For measurements on human tissues, it can be expected that the target under examination may have non-uniform boundaries and is prone to motion artifacts. For example, this certainly would be the case involving non-contact assessments of the breast. The breast is a deformable structure. Its external geometry varies with orientation of the subject, and presence of supporting structures. In addition, it can be expected that respiration and cardiac activity will introduce uncertain artifacts.

These types of variables can be problematic in terms of achieving high quality images. Motion artifacts serve as a source of noise in the measurement data, degrading image quality. While the methodology of Barbour '355 is capable of evaluating structures having non-uniform boundaries, the numerical methods applicable to problems of the type (e.g., finite differences, finite element solvents) are more efficient when the external boundary is smooth and regular (e.g., a cylindrical, hemispherical geometry). This is especially true for the case involving iterative solutions to the inverse problem, where use of multi-grid forward solvers could greatly reduce computation times. Accordingly, the present invention addresses the need to minimize motion artifacts and simultaneously conform the external geometry of a target structure to a simple shape. Because the measurement apparatus is geometrically adaptive, assessments on a variety of body structures are possible.

In summary, the apparatus described herein provides improved signal fidelity compared to prior art optical scanners. In the preferred embodiment of the invention, the conformal structure comprises a fiber optic-based tomographic assembly housed within an adjustable multi-layer iris frame that can bring multiple optical fibers in direct contact with the skin while imposing only light to moderate compression of the body tissue. This design serves several useful purposes. It acts to mechanically stabilize the tissue structure during data acquisition, thereby minimizing motion artifacts. In certain circumstances, it also causes the tissue to assume the geometry of the iris openings. This permits improved signal collection while simultaneously enabling precise knowledge of the location of the optical fibers in relation to the geometry of the target medium. By adjusting the opening of each of the multi-layer irises in relation to the tissue geometry, precise contouring to non-uniform body structures (e.g., the breast) can be achieved. The overall iris assembly is rigidly housed within a larger frame that serves to block ambient light and can be filled with scattering fluid to permit improved boundary matching.

The apparatus and system disclosed herein enable practical NIR optical tomographic imaging studies of thick tissue structures for the detection and imaging of various pathological states (e.g., cancer diagnosis and staging, evaluation of oxygen deficient states, vascular pathology, etc.) using a low-cost optical scanner. In addition, the system puts to use the fundamental concepts of the Barbour '355 patent while refining them to allow high precision, high sensitivity measurements of nonuniform geometries.

The new system is also highly flexible and, as already noted, can be easily adapted for evaluation of various body extremities of an adult (e.g., breast, limbs, genitals, head and neck) and, potentially, for evaluation of the total body volume of an infant. The system can also be adapted for veterinary uses, e.g., for the evaluation of limbs and joints of animals, such as champion race horses.

The described unit is light-weight, compact, has modest power requirements and employs low-cost optical sources and detectors. In addition, tomographic data collection is achieved with a minimal amount of mechanized operation. Production units are expected to easily fit on a laboratory cart. Minor modifications may be required for alternative embodiments, such as single vs. multi-wavelength optical and fluorescence measurements and dual-head units. The scope of this invention is not limited to the medical field and may encompass any application involving the three-dimensional imaging of objects embedded in turbid media, for example remote inspection of food products.

An advantage of the invention is recognition of the sensitivity of image accuracy and stability to errors in knowledge of the external tissue geometry, location of sources and detectors, and sensitivity to motion artifacts.

A further advantage of the invention is that various optical (laser) sources can be employed to couple NIR light into the optical fibers.

Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. An apparatus for optical tomographic imaging of tissue structures with non-uniform surface geometries, comprising:
    an optical source capable of providing light having a wavelength capable of at least attenuated transmission through the tissue;
    a first fiber array including fiber bundles for transmitting light from the optical source to the tissue to be imaged;
    a second fiber array including fiber bundles for receiving light scattered by the tissue;
    an adjustable assembly including an adjustable support member supporting one end of each fiber bundle, the fiber bundles being from the first and second fiber array and being distributed along the portion of each support member which conforms to a surface of a specimen being imaged so as to transmit light into, and collect light emanating from, the surface of the imaged tissue at a multitude of spaced-apart points; and
    a detector array receiving primarily steady-state scattered light collected by the fibers in the second fiber bundle, an output of the detector array that corresponds to the steady-state scattered light useable as a variable in a radiation transport equation.

2. The apparatus of claim 1 wherein the optical source is selected from the group consisting of: diode lasers, Ti:Sapphire lasers, dye lasers, multi-wavelength lasers, continuous-wave (CW) lasers, and pulsed-power lasers.

3. The apparatus of claim 2 wherein the optical source emits light in the near infrared portion of the electromagnetic spectrum.

4. The apparatus of claim 1 wherein the fiber array has translatable light-receiving ends adjacent to the light source.

5. The apparatus of claim 1 further comprising a focusing lens disposed between the optical source and the fiber array.

6. The apparatus of claim 1 wherein the support members are constructed of deformable material.

7. The apparatus of claim 1 wherein the support members comprise adjustable irises.

8. The apparatus of claim 1 further comprising an attenuator disposed between the fiber bundles which transmit light away from the adjustable assembly and the detector array.

9. The apparatus of claim 8 wherein the attenuator comprises:
    an inner cylinder housing the fiber bundles from the adjustable assembly;
    an outer cylinder housing the fiber bundles that direct light to the detector array; and
    a plurality of attenuators disposed between the inner and outer cylinders.

10. The apparatus of claim 9 wherein the plurality of attenuators comprise neutral density filters having a respective plurality of density values.

11. The apparatus of claim 9 wherein the plurality of attenuators comprise polarizers.

12. The apparatus of claim 1 further comprising a reference detector for monitoring the optical source from a portion of the fiber array receiving light from the optical source.

13. The apparatus of claim 1 further comprising an outer housing enclosing the adjustable assembly wherein the outer housing excludes ambient light.

14. The apparatus of claim 13 wherein the outer housing further comprises a rubber dam for containing submersive index-matching fluid.

15. The apparatus of claim 1 wherein the detector array is a charge-coupled device (CCD) detector array.

16. The apparatus of claim 15 wherein there is a fixed physical relationship between the detector array and the attached ends of the fiber bundles which transmit light away from the adjustable assembly.

17. The apparatus of claim 1 further comprising a second adjustable assembly to form a dual-head scanner.

18. The apparatus of claim 8 wherein the attenuator further comprises a wavelength-selective filter.

19. The apparatus of claim 1 wherein the fiber bundles comprise multiple small-diameter fibers, each with a diameter of less than 200 microns, and wherein the fiber bundles each have a total active surface area of at least 2 square millimeters.

20. The apparatus of claim 19 wherein there is a minimum of 100 fiber bundles.

21. The apparatus of claim 1 further comprising computing means for three-dimensional image reconstruction and display of data received from the detector array.

22. A method of optical tomographic imaging of tissue structures with non-uniform surface geometries, comprising:

using an adjustable assembly to snugly conform to the geometry of a specimen under test;

illuminating the specimen with light from a source via transmitting fiber bundles contained within the adjustable assembly;

collecting primarily steady-state scattered light from the specimen at the source wavelength using receiving fiber bundles contained within the adjustable assembly;

detecting the steady-state scattered light with a detector array;

analyzing an output of the detector array that corresponds to the steady-state scattered light as a variable in a radiation transport equation with a computer capable of constructing and displaying a three-dimensional image from the steady-state scattered light.

23. The method of claim 22 wherein the steady-state scattered light from the specimen is at a wavelength other than the source wavelength.

24. The method of claim 22 wherein the specimen is illuminated at a plurality of source wavelengths.

25. The method of claim 22 further comprising monitoring the source light by diverting a portion of the source light to a reference detector.

26. The method of claim 22 further comprising selectively attenuating the steady-state scattered light from the specimen.

27. The method of claim 22 further comprising excluding ambient light from the adjustable assembly by enclosing the adjustable assembly with an outer housing.

28. The method of claim 27 further comprising index matching the specimen under test by filling the outer housing with index matching fluid.

29. The method of claim 22 further comprising using two adjustable assemblies to form a dual-head scanner.

30. The method of claim 22 further comprising using a wavelength-selective filter.

31. The method of claim 22 further comprising using fiber bundles comprising multiple small-diameter fibers, each with a diameter of less than 200 microns, and wherein the fiber bundles each have a total active surface area of at least 2 square millimeters.

32. The method of claim 31 further comprising using a minimum of 100 fiber bundles.

* * * * *

UNITED STATES PATENT AND TRADEMARK OFFICE
CERTIFICATE OF CORRECTION

PATENT NO.: 6,081,322

DATED: June 27, 2000

INVENTOR(S): Randall L. Barbour

It is certified that errors appear in the above-identified patent and that said Letters Patent is hereby corrected as shown below:

On the Title page:
  Item [75], change "Westbury" to -- Glen Head --
  Item [73], before "Research" insert -- The --; and after "State" insert -- University --

Signed and Sealed this

Seventeenth Day of April, 2001

Attest:

NICHOLAS P. GODICI

Attesting Officer    Acting Director of the United States Patent and Trademark Office